(12) United States Patent
Frazier et al.

(10) Patent No.: US 6,932,091 B2
(45) Date of Patent: Aug. 23, 2005

(54) METHOD FOR SURGICALLY RESTORING CORONARY BLOOD VESSELS

(76) Inventors: O. Howard Frazier, 3311 Richmond, #350, Houston, TX (US) 77097; Stephen R. Igo, 526 Birdsong, League City, TX (US) 77573

( * ) Notice: Subject to any disclaimer, the term of this patent is extended or adjusted under 35 U.S.C. 154(b) by 212 days.

(21) Appl. No.: 10/618,897

(22) Filed: Jul. 14, 2003

(65) Prior Publication Data

US 2004/0098103 A1 May 20, 2004

Related U.S. Application Data

(62) Division of application No. 09/860,805, filed on May 18, 2001, now abandoned.

(51) Int. Cl.$^7$ ............................................. A61B 19/00
(52) U.S. Cl. ...................................... 128/898; 606/153
(58) Field of Search .......................... 128/898; 623/1.1, 623/1.11; 604/8; 606/152–159, 200, 190–182, 194–195

(56) References Cited

U.S. PATENT DOCUMENTS

| | | | | |
|---|---|---|---|---|
| 5,755,682 A | * | 5/1998 | Knudson et al. | 604/8 |
| 6,090,135 A | * | 7/2000 | Plaia et al. | 623/1.11 |
| 6,409,750 B1 | | 6/2002 | Hyodoh et al. | 623/1.1 |

* cited by examiner

*Primary Examiner*—Tan-Uyen T. Ho
(74) *Attorney, Agent, or Firm*—Tim Headley; Gardere Wynne Sewell LLP (57) ABSTRACT

A method for surgically restoring a coronary artery having an atheroma, to more normal structure by making an arteriotomy incision over the length of the atheroma, extracting plaque, inserting stent into the coronary artery at the incision and closing the coronary artery over the stent with sutures. An extravascular drug delivery material is applied over the stent implantation site to inhibit thrombosis and smooth muscle cell proliferation.

6 Claims, 6 Drawing Sheets

METHOD FOR SURGICALLY RESTORING CORONARY BLOOD VESSELS

CROSS-REFERENCE TO RELATED APPLICATIONS

This application is a divisional of pending application Ser. No. 09/860,805, now abandoned bearing the same title.

STATEMENT REGARDING FEDERALLY SPONSORED RESEARCH OR DEVELOPMENT

Not Applicable.

REFERENCE TO A "SEQUENTIAL LISTING," A TABLE, OR A COMPUTER PROGRAM LISTING APPENDIX SUBMITTED ON A COMPACT DISC

Not Applicable.

BACKGROUND OF THE INVENTION

Coronary artery disease is the leading cause of death and disability in the major industrialized countries of the world. Treatment of advanced atherosclerotic coronary artery disease, beyond that amenable to therapy via medication alone, now generally includes interventional cardiology procedures in the form of Percutaneous Transluminal Coronary Angioplasty (PTCA) or cardiovascular surgery procedures in the form of Coronary Artery Bypass Grafting (GABG).

The PTCA technique involves the retrograde introduction from an artery in the leg or arm, of a catheter with a small dilating balloon at its tip. The catheter is advanced through the arteries by fluoroscopic guidance and is passed across the luminal narrowing of the coronary artery over a guide wire. Once in place, the catheter balloon is inflated for a short period of time. This results in mechanical deformation of the atherosclerotic plaque or the vessel wall with a subsequent increase in the cross-sectional area of the artery. This in turn reduces vessel obstruction and transluminal pressure gradients, and increases blood flow through the coronary artery.

PTCA or angioplasty is a term that now may include other percutaneous transluminal methods of decreasing stenosis within a coronary blood vessel besides balloon dilation alone. These methods include: lumen expansion with an endoluminal stent that prevents elastic recoil of the vessel; mechanical atherectomy with shaving, extraction, thermal ablation or ultrasonic pulverization of the lesion; and methods of endoluminal drug delivery or radiation treatment. Mechanical atherectomy may result in incomplete plaque removal, particularly in the side branch vessels of the artery, and/or embolization of plaque debris to the downstream coronary circulation. In addition, it is difficult, and sometimes impossible to provide complete coronary revascularization with PTCA techniques for patients with total vessel occlusions, long obstructions, or diffuse lesion sites. During the year 2000, approximately 1.4 million patients worldwide underwent PTCA procedures.

The CABG technique involves placing the patient on cardiopulmonary bypass (heart-lung machine), and temporarily stopping the heart muscle. Surgery is then affected on the coronary arteries in the form of bypass conduit vessels using vein or artery grafts from the aorta to the coronary artery distal to the lesion sites, thereby providing blood flow around the obstructions. Compared to PTCA procedures, CABG surgery provides more complete revascularization for patients with multi-vessel coronary artery disease. During the year 2000, it is estimated that 1 million patients underwent CABG surgery worldwide.

The profile of patients undergoing CABG surgery is continuously changing. Today, patients being referred for CABG surgery are older, and many have undergone previous revascularization procedures. Therefore, the number of patients having severe and diffuse coronary disease has been increasing. Diffuse multi-vessel coronary artery disease is a challenge for surgeons, precluding complete revascularization in some patients, while rendering others inoperable. Incomplete revascularization is one of the most important variables, affecting both operative and late mortality following CABG surgery. In particular, residual disease of the left anterior descending (LAD) artery has been shown to adversely affect patient survival. Recently, the application of new revascularization procedures, aimed at growing new coronary blood vessels using laser devices or angiogenesis drugs, has refocused attention on the surgical management of diffuse coronary artery disease. For patients with total vessel occlusions, long obstructions, or severe diffuse coronary disease, an endarterectomy procedure (removal of the atherosclerotic plaque) may be the only option that can produce good clinical results in otherwise inoperable situations.

Surgical endarterectomy of the right coronary artery (RCA) requires a different technique from that used for the LAD. The RCA and its atheromatous core are of a large caliber, thick, and strong. Further, the main RCA trunk and its major branches (the posterior descending and the posterolateral vessels) are in the same geometric plane. Therefore, RCA endarterectomy can usually be accomplished by the traction-counter-traction technique with or without mechanical assistance (i.e. gas dissection of the lesion from the vessel wall) through a relatively short vessel incision (arteriotomy).

In contrast, the LAD atheromatous core is narrow and delicate, and its thickness is usually uneven, being thicker and stronger near vessel bifurcations, and thinner in between the side branches, increasing the risk of plaque disruption under tension. Furthermore, the LAD artery has many branches that come off at two different geometric planes 90° apart (the septal and diagonal branches). When traction is applied to the atheromatous LAD core directed at extracting one set of branch vessels it exerts a sheering force on the other side branches, breaking the plaque off, and occluding the vessels ("snowplow effect"). Therefore, endarterectomy of the LAD artery should be done through a long arteriotomy incision that allows for the complete removal of atheromatous plaque from the main vessel and side branches under direct vision. Following endarterectomy, a vein patch is often required to close the artery before the distal bypass graft anastomosis can be performed.

Despite the major therapeutic advances in the treatment of coronary artery disease provided by PTCA interventions and CABG surgery, the long-term success of these procedures has been hampered by the development of vessel re-narrowing or re-closure. Abrupt vessel occlusion may develop during a period of hours to days post-procedure, due to vasospasm and/or thrombosis at the site of vessel injury. The most common and major limitation, however, is the development of progressive reversion of the diseased vessel to its previous stenotic condition, negating any gains achieved from the procedure. This gradual re-narrowing process is most commonly due to vessel constriction and/or to intimal hyperplasia, and is referred to as restenosis. Restenosis is generally believed to be a normal reparative response to endovascular injury after angioplasty, and in vein grafts following vessel bypass surgery. The sequence of events is similar for PTCA and CABG restenosis, progressing through the process of vasoconstriction, thrombus formation and organization, growth factor and cytokine release, and smooth muscle cell proliferation.

Clinical follow-up studies indicate that significant vessel restenosis occurs in about 40% of balloon angioplasty patients and in about 25% of the PTCA/stent patients within six months, and in about 20% of the CABG patients within one year. This complication of vessel restenosis results in increased patient morbidity, need for repeating the procedure, and escalating medical costs. With an estimated 2,400,000 PTCA and CABG procedures performed worldwide in 2000 for coronary artery revascularization, these percentages of restenosis mean as many as 640,000 patients may develop vessel restenosis within one year after operation. Thus, repeat procedures could account for over $9 billion in additional healthcare costs, which increase each year.

1. Field of the Invention

The present invention relates generally to methods and devices for performing coronary artery revascularization surgery. More specifically, it relates to methods and devices for repairing partially blocked coronary arteries, including the use of stents.

2. Description of Related Art

Coronary artery stents are known in the prior art. There are two broad groups of endocoronary stent devices: 1) balloon expandable and 2) self-expanding. Within these groups, there is substantial variability with regards to manufacturing techniques, materials, architecture, dimensions, surface coatings (i.e., drugs, radiation, or other biological material), and strut configurations. However, these stents, used only by cardiologists and not by cardiovascular surgeons, cannot be implanted in a coronary artery at the site of a major side branch vessel, because the stent may block or occlude the opening of the side branch vessel. Often the diseased area of a coronary artery is several centimeters in length, from which there are several side branch vessels, particularly for the LAD.

Drug delivery stents designed to inhibit stent thrombosis and intimal hyperplasia, termed restenosis, are known in the prior art. Drug delivery stents may not be completely effective, however, because of low tissue drug levels, drug washout into the blood stream, inflammatory response caused by the drug eluting coating, and increased stent dimensions due to coating thickness.

Thus, there is a need for improving the way coronary artery revascularization surgery is performed, that results in more complete and durable outcomes for patients, physicians, and healthcare delivery systems.

BRIEF SUMMARY OF THE INVENTION

A preferred embodiment of the present invention provides for a surgical method to treat long stenosis within a coronary artery, preferably the left anterior descending coronary artery, the circumflex coronary artery and branches, and the right coronary artery. The surgical method, open endarterectomy, involves performing an extended arteriotomy incision over the entire length of the lesion, with removal of atherosclerotic plaque from the side branches of the diseased coronary blood vessel. Another feature of the preferred method allows for treatment of the occlusive lesion regardless of length and composition.

Another preferred feature of the present invention allows for closure of the long arteriotomy with sutures over a catheter of calibrated diameter and length. The catheter is gradually removed from the vessel during closure. Another feature of the invention allows for the coronary catheter to be used for the endocoronary seeding of autologous cells harvested from the patient. Cell seeding is intended to enhance healing and re-growth of the vessel lining. The endoluminal catheter may also be used for local injection of vasoactive drugs during vessel closure. Drugs include, but are not limited to, vasodilator nitric oxide donor drugs such as nitroglycerin and sodium nitroprusside, or prostacyclin donor drugs such as alprostadil. These drugs, given alone or in combination, are intended to prevent vessel spasm during coronary artery closure.

Another feature of the present invention provides for a surgical method to remove atherosclerotic plaque from a diseased coronary artery, and then to implant a pre-expanded stent device into the coronary artery with subsequent suture closure of the artery over the endocoronary stent. In one preferred embodiment, the endocoronary stent maintains an optimal vessel diameter, and prevents over-sewing of the vessel walls. Another feature of the present invention provides for an open-ended (non-circumferential), rib-like endocoronary stent having anchor prongs attached to the stent rib for fixation to the vessel wall. The anchor prongs provide a means for increasing the radial strength of the stent, and preventing stent compression and collapse.

Another feature of the present invention provides for an open-ended (non-circumferential), rib-like endocoronary stent having a textured luminal surface.

Another feature of the present invention is a method and product for extravascular topical drug delivery directly to the coronary artery surgery site. The drug delivery method and product includes one or more drugs, including gene therapy agents, with a controlled release rate without systemic side effects, for use in conjunction with the endocoronary stent, to limit or prevent the development of stent thrombosis and intimal hyperplasia.

BRIEF DESCRIPTION OF THE DRAWINGS

The present invention may be more completely and easily understood when taken in conjunction with the accompanying line drawings, in which.

DETAILED DESCRIPTION OF THE INVENTION

Figure 1:
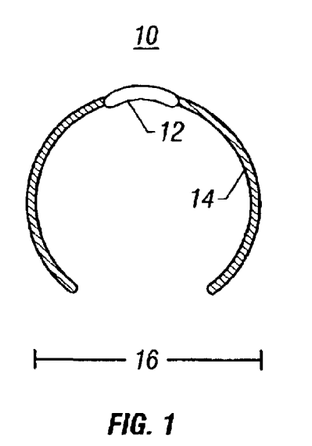
FIG. 1 is an enlarged cross-sectional end view of a pre-expanded surgically implanted endocoronary stent manufactured according to a preferred embodiment of the present invention.
Figure 2A:
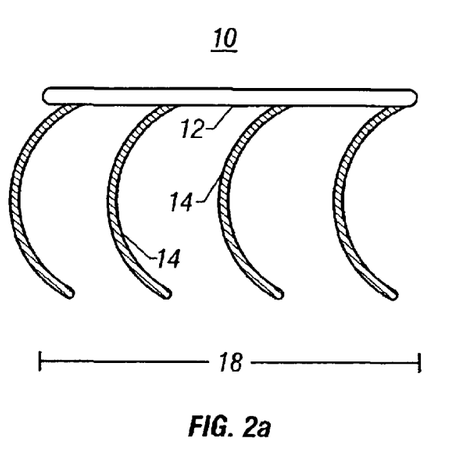
FIG. 2a is a side view of the pre-expanded endocoronary stent shown in FIG. 1.
Figure 2B:
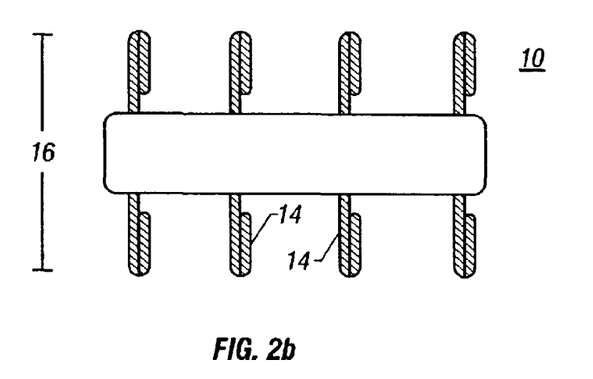
FIG. 2b is a top view of the pre-expanded endocoronary stent shown in FIG. 1.

In the drawings, like numerals designate like parts throughout the drawings. In FIG. 1, a pre-expanded surgically implanted endocoronary stent 10 includes a spine member 12 having a rib 14. The rib 14 is circular in shape, and encompasses 75% of the stent 10 circumference. The endocoronary stent 10 is 316L stainless steel or tantalum wire, having a thickness of 0.12 mm. The endocoronary stent 10 has a diameter 16 of any one of the following sizes: 2.5 mm, 3.0 mm, 3.5 mm, 4.0 mm, 4.5 mm, and 5.0 mm. Referring to FIG. 2a, the pre-expanded endocoronary stent 10 has a length 18 of any one of the following sizes: 20 mm, 40 mm, or 60 mm. Referring to FIG. 2b, the endocoronary stent 10 has four ribs 14. The endocoronary stent 10 has a textured surface, which may be polymeric or a powdered metal. The textured surface provides a bonding matrix for enhanced cell seeding of the endocoronary stent with autologous endothelial cells.

Figure 3:
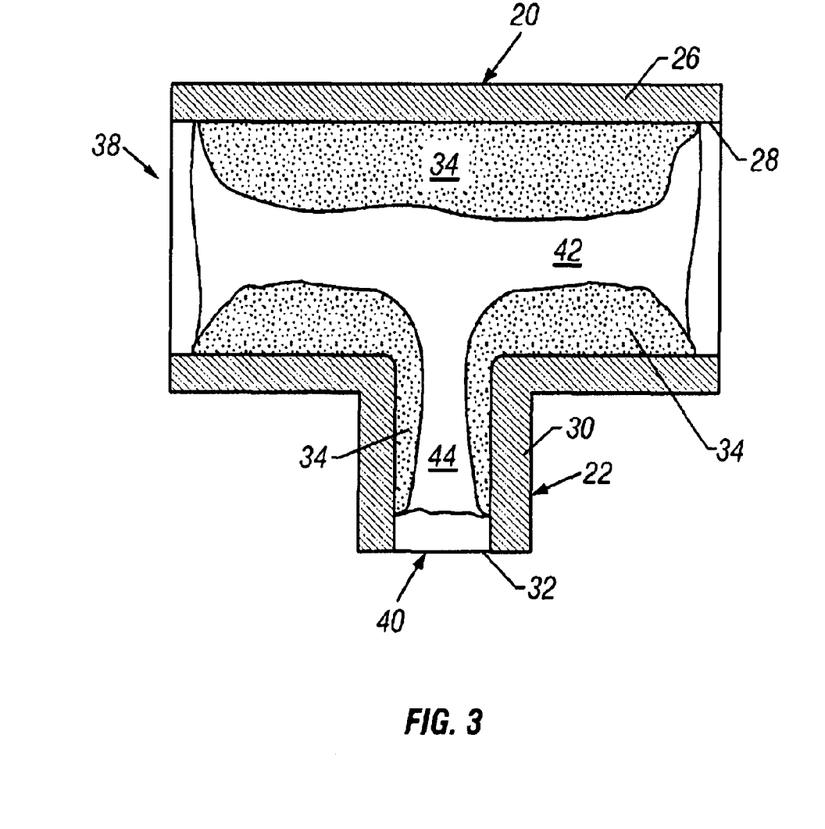
FIG. 3 is an enlarged cross-sectional side view drawing of a diseased and occluded epicardial coronary artery, and perforating side branch vessel in a patient.
Figure 4:
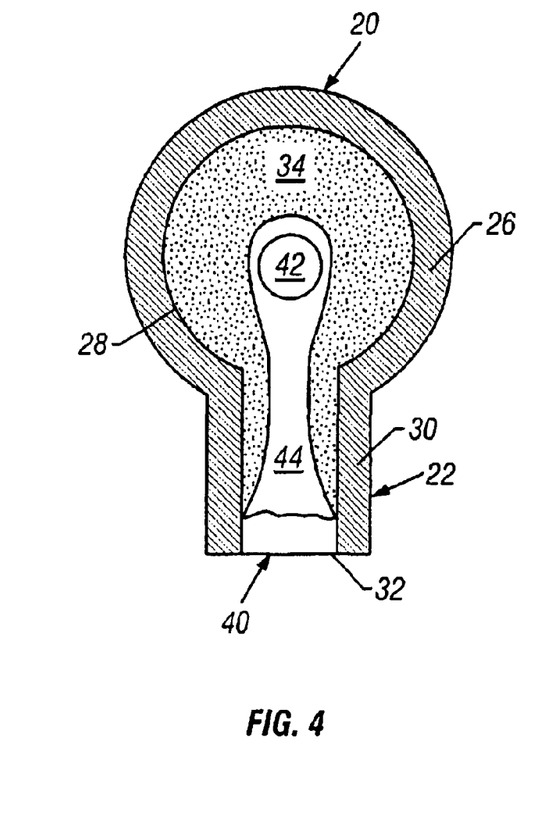
FIG. 4 is an enlarged cross-sectional end view through the side branch of the diseased coronary artery shown in FIG. 3.

Referring to FIG. 3, a diseased and occluded epicardial coronary artery 20 has a perforating side branch vessel 22. A wall of the epicardial coronary artery 20 consists of outer media and adventitia layers 26, which are composed of smooth muscle cells and connective tissue, and an inner intima layer 28, which is normally lined by endothelial cells. Likewise, the wall of the perforating side branch vessel 22 consists of media and adventitia layers 30, and an inner intima layer 32. Atherosclerotic plaque 34 most commonly consists of calcific, fibrous or mixed composition material. The atherosclerotic plaque 34 commonly extends into the side branch vessel 36. The area with the plaque 34 is referred to as an atheroma. FIGS. 3 and 4 illustrate the diameters of normal, non-diseased, blood vessel lumens 38, 40, and stenosed vessel lumens 42, 44 of the epicardial coronary artery 20 and side branch vessel 22, respectively.

Figure 5:
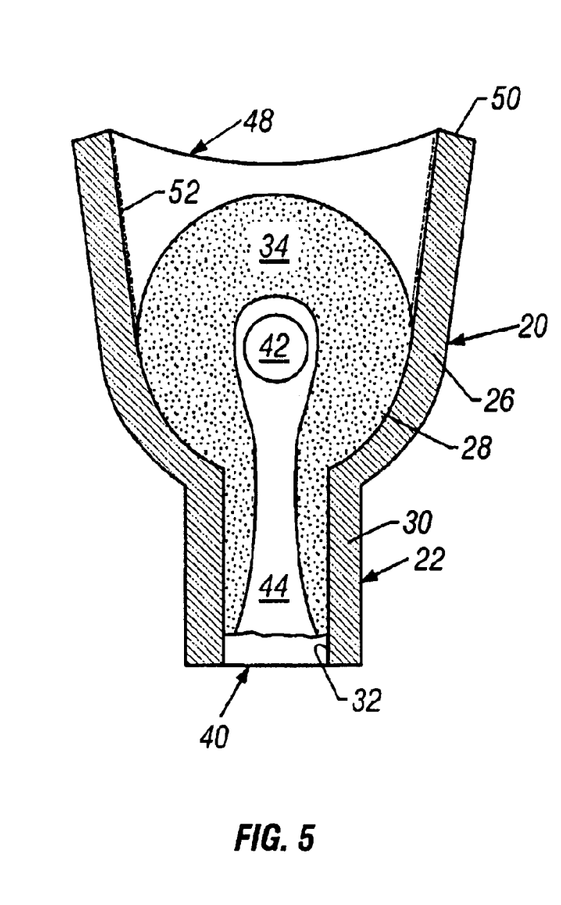
FIG. 5 is a cross-sectional end view of the diseased coronary artery showing a long arteriotomy with exposure of the atherosclerotic plaque.
Figure 6:
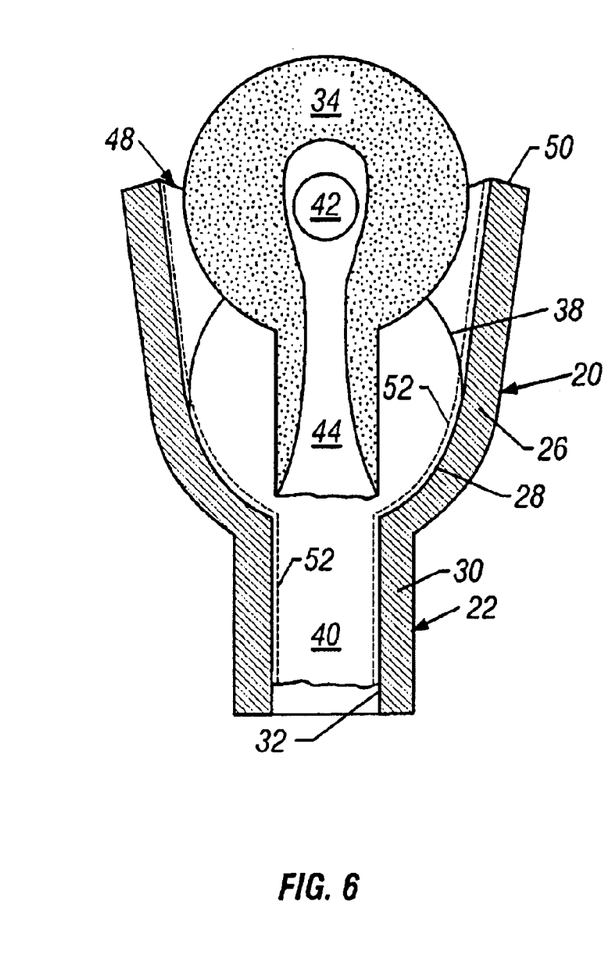
FIG. 6 is a cross-sectional end view of the diseased coronary artery illustrating complete extraction of the atherosclerotic plaque including side branch plaque through the long arteriotomy.

Referring to FIG. 5, the epicardial coronary artery 20 and perforating side branch vessel 22 have been surgically opened by the surgeon with a long arteriotomy incision 48. The atherosclerotic plaque 34 is exposed by spreading the cut edges of the arteriotomy 50, and separating the plaque 34 from the medial interface of the vessel wall 52. Referring to FIG. 6, the surgeon extracts the atherosclerotic plaque 34 from the epicardial artery 20, and from the side branch artery 22. This extraction of plaque is referred to as an endarterectomy.

Figure 7:
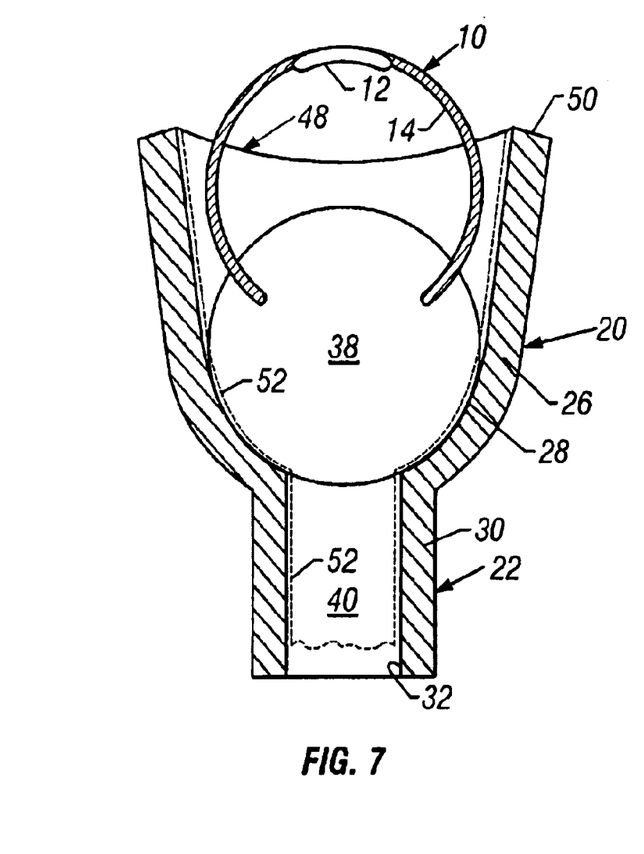
FIG. 7 is a cross-sectional end view of the coronary artery following plaque removal showing insertion of a pre-expanded endocoronary stent, as shown in FIG. 1, through the long arteriotomy, into the blood vessel lumen.
Figure 8:
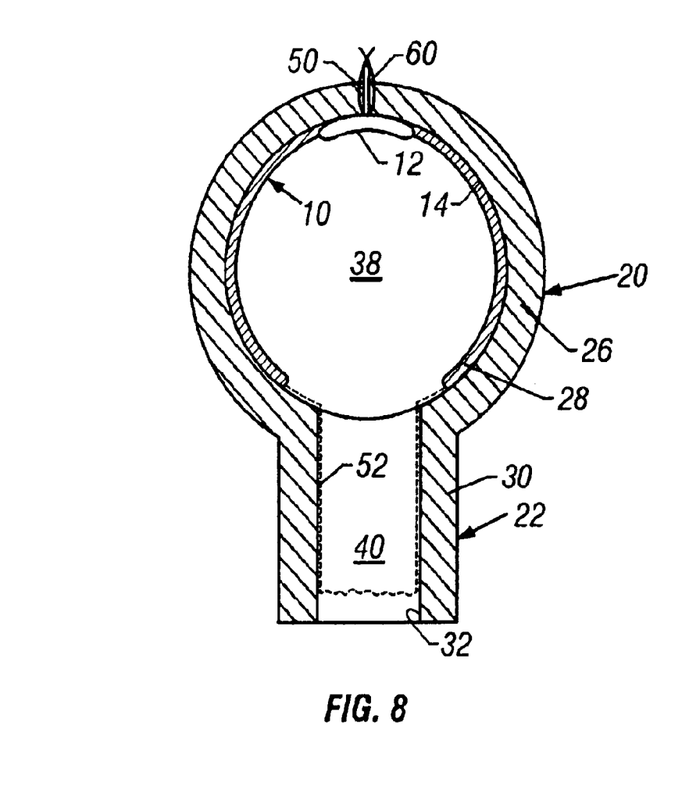
FIG. 8 is a cross-sectional end view of the coronary artery following implantation of the stent device and suture closure of the arteriotomy over the stent.

Referring to FIG. 7, following plaque removal, the surgeon inserts the pre-expanded endocoronary stent 10 through the arteriotomy 48. Referring to FIG. 8, the surgeon closes the arteriotomy incision 50 over the pre-expanded endocoronary stent 10 by sutures 60. This closure is referred to as anastomosis.

Figure 9:
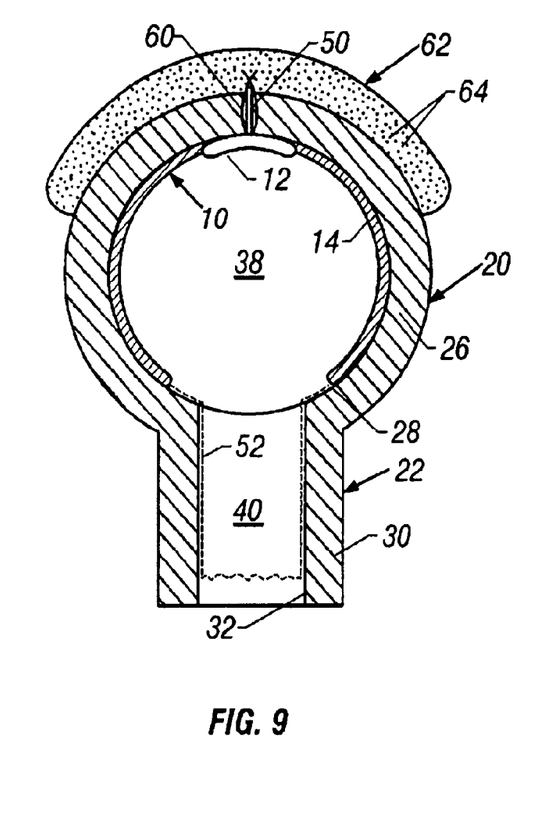
FIG. 9 is a cross-sectional end view of the coronary artery with surgically implanted endocoronary stent and extravascular drug delivery implant.
Figure 10:
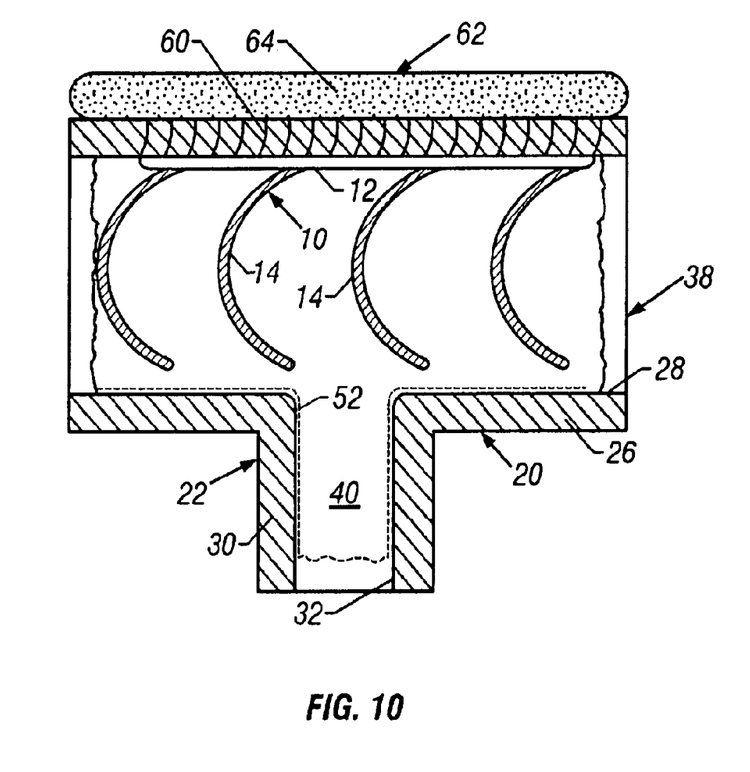
FIG. 10 is a cross-sectional side view of the coronary artery with surgically implanted endocoronary stent and extravascular drug delivery implant.

Referring to FIG. 9 and FIG. 10, a perivascular drug delivery matrix 62 is applied over the anastomosis 60. The matrix may consist of a non-biodegradable polymer (for example, polyurethane, silicone), a biodegradable polymer (i.e., poly-L-lactic acid), or an absorbable biopolymer (for example, fibrin). The extra-coronary matrix is loaded with a bioactive agent 64 providing local controlled drug release. Cardiovascular drugs for extravascular delivery can include vasodilator, antiplatelet antimitotic, angiogenic and gene therapy agents. The duration for controlled drug release can range from 3 to 14 days. The drugs may be of any type which would be useful in preventing acute vessel thrombosis, antiplatelet, and/or antithrombotic agents inhibiting chronic restenosis of the vessel, antimitotic agents to limit smooth muscle cell proliferation, and promoting endothelial cell growth. U.S. Pat. Nos. 5,681,278 and 5,900,433, the disclosures of which are incorporated by reference, describe known methods for forming extracoronary artery drug delivery implants that are suitable for this invention.

Figure 11:
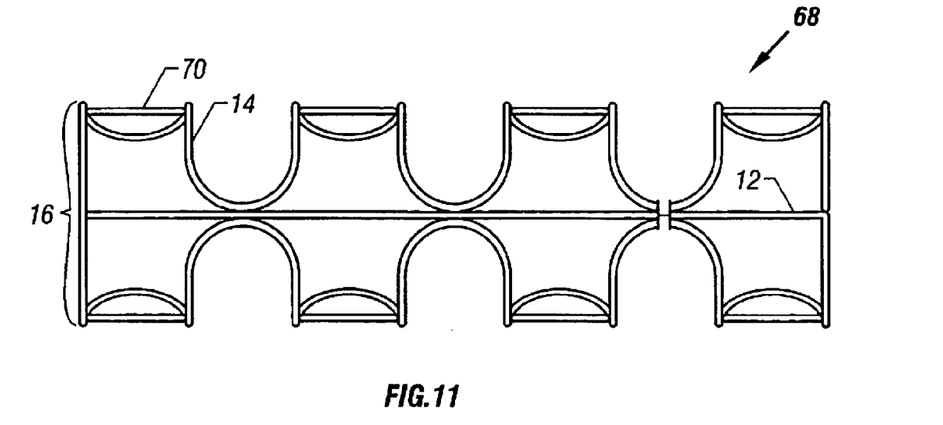
FIG. 11 is an enlarged cross-sectional top view of a pre-expanded endocoronary stent with vessel anchor prong, according to a preferred embodiment of the present invention.

In FIG. 11, a pre-expanded surgically implanted endocoronary stent 68 includes vessel anchor prongs 70 attached to the stent ribs 14 for fixation to the vessel wall. The anchor prong 70 provides a means for increasing the radial strength of the stent 68, and preventing stent compression and collapse. The rib 14 is circular in shape, encompasses 75% of the stent 68 circumference, and attaches to the spine 12. The endocoronary stent 68 is a 316L stainless steel, or Elgiloy alloy, or tantalum wire, having a thickness of 0.12 mm. The endocoronary stent 68 has a diameter 16 of any one of the following sizes: 2.5 mm, 3.0 mm, 3.5 mm, 4.0 mm, 4.5 mm, and 5.0 mm.

The endocoronary stent 68 is radially non-compressible, and axially semi-flexible, having minimal material volume and mass. The endocoronary stent 68 has a low profile when implanted into the vessel lumen, and is designed not to occlude or obstruct the coronary artery side branches. The endocoronary stent 68 is radiopaque and biocompatible for long-term implantation with minimal trauma to the vessel wall.

Figure 12:
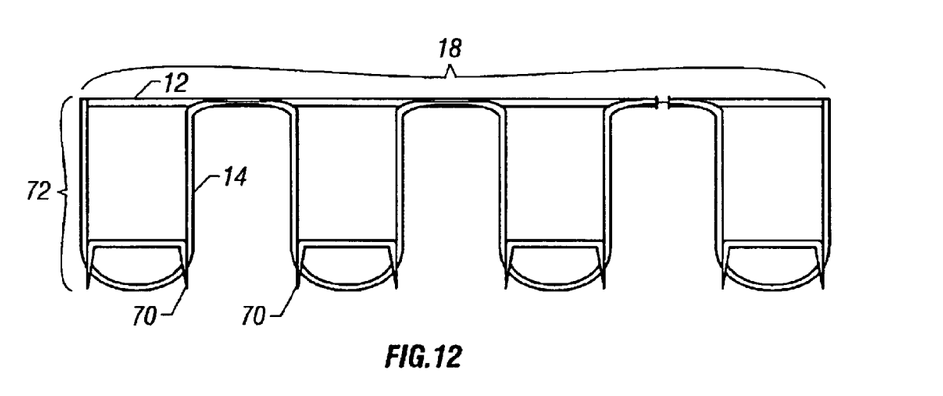
FIG. 12 is a side view of the pre-expanded endocoronary stent with vessel anchor prong shown in FIG. 11.
Figure 13:
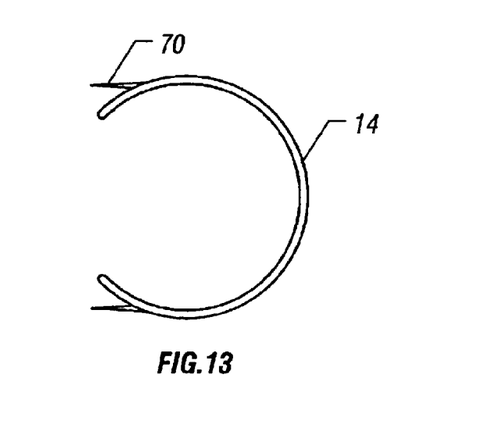
FIG. 13 is an enlarged side view of the stent anchor prong shown in FIG. 11.

Referring to FIG. 12, the pre-expanded endocoronary stent 68 has a stent height 72, which is equal to 85% of the stent diameter 16, and has a manufactured length 18 of any one of the following sizes: 25 mm, 50 mm, or 75 mm. The number of stent ribs 14 is equal in number (N) to stent length 18 divided by 5 (i.e., 5, 10, and 15 N for lengths of 25 mm, 50 mm, and 75 mm, respectively). Rib 14 diameter (D1) is equal to stent length 18 divided by rib number (N)−1. For example, for 50 mm stent length, D1=50/(10−1)=5.56 mm. FIG. 13 is an enlarged side view of the stent rib 14 and a vessel anchor prong 70. The anchor prong 70 is laser welded to alternating ribs 14. The length of the prong between the ribs=D1−wire thickness of 0.12 mm. The length of the prong for implantation into the vessel wall for fixation=10% of the stent diameter 16 times 3.1415. For example, for a 4 mm stent diameter, prong length=0.1(4×3.1415)=1.26 mm.

In summary, the present invention is both an apparatus and a method, which includes the following steps:

a. performing an extended arteriotomy over the length of the coronary artery atheroma;

b. spreading the cut edges of the arteriotomy incision;

c. separating the plaque from the medial interface of the vessel wall;

d. extracting the atherosclerotic plaque from the epicardial artery, and from any side branch artery;

e. inserting a pre-expanded stent device with vessel anchor prong, of calibrated diameter, length, and curvature, into the opened-artery lumen;

f. closing the coronary artery over the stent with sutures; and g. treating the coronary artery surgery site with a drug delivery material, extravascular to the stent implantation site, for local controlled release of bioactive factors to inhibit both thrombosis and smooth muscle cell proliferation.

This procedure may be performed on the non-beating heart during cardiopulmonary bypass, or on the beating unloaded heart with the aid of a heart bypass system. The procedure may also be performed on the heart ex vivo with the aid of cardiopulmonary bypass followed by autotransplantation.

The present invention provides a method and apparatus for restoring the structure and function of a diseased coronary blood vessel. Other blood vessels can also be surgically treated and stented without departing from the scope of the present invention. The invention is not intended to be limited to the specifics of the described preferred embodiments, but is defined by the accompanying claims.

What is claimed is:

1. A method for surgically restoring a coronary artery having an atheroma, to more normal structure and function, comprising the steps of:

a. making an arteriotomy incision over the length of the atheroma;

b. extracting atherosclerotic plaque from the atheroma;

c. inserting a pre-expanded endocoronary stent into the coronary artery at the incision; and d. closing the coronary artery over the stent with sutures.

2. A method for surgically restoring a coronary artery having an atheroma, to more normal structure and function, comprising the steps of:

a. making an arteriotomy incision over the length of the atheroma;

b. spreading cut edges of the arteriotomy incision;

c. extracting the atherosclerotic plaque from the coronary artery, and from any side branch artery;

d. inserting a pre-expanded endocoronary stent into the coronary artery at the incision; and e. closing the coronary artery over the stent with sutures.

3. A method for surgically restoring a coronary artery having an atheroma, to more normal structure and function, comprising the steps of:

a. making an arteriotomy incision over the length of the atheroma;

b. spreading cut edges of the arteriotomy incision;

c. separating the plaque from the medial interface of a vessel wall of the coronary artery;

d. extracting the atherosclerotic plaque from the coronary artery, and from any side branch artery;

e. inserting a pre-expanded endocoronary stent into the opened coronary artery; and f. closing the coronary artery over the stent with sutures.

4. A method for surgically restoring a coronary artery having an atheroma, to more normal structure and function, comprising the steps of:

a. making an arteriotomy incision over the length of the atheroma;

b. spreading cut edges of the arteriotomy incision;

c. separating atherosclerotic plaque from a medial interface of a vessel wall of the coronary artery;

d. extracting the atherosclerotic plaque from the coronary artery, and from any side branch artery;

e. inserting a pre-expanded endocoronary stent into the coronary artery at the incision;

f. closing the coronary artery over the stent with sutures; and g. applying extravascular drug delivery material over the site at the stent inserted.

5. The method of claim 4, wherein the extravascular drug delivery material provides a local controlled release of bioactive factors to inhibit both thrombosis and smooth muscle cell proliferation.

6. The method of any of claims 1–5, wherein the pre-expanded endocoronary stent has calibrated diameter, length, and curvature.

* * * * *